(12) United States Patent
Schlatterer

(10) Patent No.: US 11,464,553 B2
(45) Date of Patent: *Oct. 11, 2022

(54) PRE-CONTOURED BUTTRESS PLATE FOR POSTERIOR WALL ACETABULAR FRACTURES

(71) Applicant: Daniel Robert Schlatterer, Dunwoody, GA (US)

(72) Inventor: Daniel Robert Schlatterer, Dunwoody, GA (US)

(*) Notice: Subject to any disclaimer, the term of this patent is extended or adjusted under 35 U.S.C. 154(b) by 220 days.

This patent is subject to a terminal disclaimer.

(21) Appl. No.: 17/086,334

(22) Filed: Oct. 31, 2020

(65) Prior Publication Data

US 2021/0045787 A1 Feb. 18, 2021

Related U.S. Application Data

(60) Continuation-in-part of application No. 16/294,023, filed on Mar. 6, 2019, now Pat. No. 10,864,027, which is a division of application No. 15/289,362, filed on Oct. 20, 2016, now Pat. No. 10,307,192.

(51) Int. Cl.
*A61B 17/80* (2006.01)

(52) U.S. Cl.
CPC ............................... *A61B 17/8061* (2013.01)

(58) Field of Classification Search
CPC . A61B 17/80; A61B 17/8052; A61B 17/8057; A61B 17/8061; A61B 17/8066
See application file for complete search history.

(56) References Cited

U.S. PATENT DOCUMENTS

| | | | |
|---|---|---|---|
| 6,440,131 B1 * | 8/2002 | Haidukewych | A61B 17/8066 606/907 |
| 8,603,091 B2 | 12/2013 | Lutz | |
| 8,808,333 B2 | 8/2014 | Kuster | |
| 9,204,912 B2 | 12/2015 | Price | |
| 9,271,773 B2 * | 3/2016 | Hwa | A61B 17/809 |
| 9,414,872 B2 | 8/2016 | Price | |
| 9,545,276 B2 * | 1/2017 | Buchanan | A61B 17/8061 |
| 9,597,131 B2 | 3/2017 | Price | |
| 9,668,793 B2 | 6/2017 | Gaudin | |
| 9,668,794 B2 | 6/2017 | Kuster | |
| 10,251,687 B2 | 4/2019 | Guo | |
| 10,307,192 B2 * | 6/2019 | Schlatterer | A61B 17/8061 |
| 10,758,282 B2 | 9/2020 | Li | |
| 10,864,027 B2 * | 12/2020 | Schlatterer | A61B 17/8061 |

(Continued)

*Primary Examiner* — Eric S Gibson
(74) *Attorney, Agent, or Firm* — David L. King

(57) ABSTRACT

An improved posterior acetabular wall fracture buttress plate has a main plate and a plate extension. The buttress plate has a pair of arms extending from the main plate and an arm extending from the plate extension. The main plate and the plate extension are pre-contoured with a concavity contoured and bent lengthwise off horizontal relative to the main plate to mimic a hip socket contour posteriorly along an undersurface at about 38 degrees plus or minus 8 degrees to mimic a curvature of the hip to yield an angle on the undersurface of 142 degrees plus or minus 8 degrees. The arms are 1.0 cm or less wide. The plate extension extends from the main plate and has at least one transverse groove defining a breakaway section allowing the plate extension to be removed from the main plate.

20 Claims, 5 Drawing Sheets

(56) References Cited

U.S. PATENT DOCUMENTS

| | | | |
|---|---|---|---|
| 2010/0217327 A1* | 8/2010 | Vancelette | A61B 17/8061 606/281 |
| 2010/0256687 A1* | 10/2010 | Neufeld | A61B 17/8061 606/280 |
| 2011/0137314 A1* | 6/2011 | Kuster | A61B 17/74 606/281 |
| 2012/0165878 A1* | 6/2012 | Hwa | A61B 17/809 606/280 |
| 2012/0226279 A1* | 9/2012 | Lutz | A61B 17/8066 606/281 |
| 2014/0066996 A1* | 3/2014 | Price | A61B 17/8057 606/280 |
| 2014/0180343 A1* | 6/2014 | Gaudin | A61F 2/4225 606/283 |
| 2014/0277176 A1* | 9/2014 | Buchanan | A61B 17/8057 606/280 |
| 2017/0181784 A1* | 6/2017 | Li | A61B 17/1728 |
| 2017/0319249 A1* | 11/2017 | Guo | A61B 17/80 |
| 2018/0110551 A1* | 4/2018 | Schlatterer | A61B 17/8061 |
| 2019/0201063 A1* | 7/2019 | Schlatterer | A61B 17/8061 |
| 2021/0045787 A1* | 2/2021 | Schlatterer | A61B 17/809 |

\* cited by examiner

PRE-CONTOURED BUTTRESS PLATE FOR POSTERIOR WALL ACETABULAR FRACTURES

RELATED APPLICATIONS

The present application is a continuation in part of U.S. application Ser. No. 16/294,023 filed on Mar. 6, 2019 which is a division of U.S. Ser. No. 15/298,362 filed on Oct. 20, 2016 now U.S. Pat. No. 10,307,192 issued on Jun. 4, 2019 entitled, "Pre-Contoured Buttress Plate For Posterior Wall Acetabular Fractures".

TECHNICAL FIELD

The present invention relates to a faster safer and less costly method of stabilizing a fracture of the acetabulum (hip socket).

BACKGROUND OF THE INVENTION

Often bone fractures are reduced surgically and the fracture fragments are immobilized by a metal plate which spans the fracture and has screws going into the plate on either side to secure the fracture fragments while also securing reduction of the fracture so that anatomic healing of the fracture can occur by new bone growth. Ideally, fractures mend in three months or less. In some cases healing takes up to one year. It is therefore essential the repaired fracture stays held securely together for at least the typical three months, if not longer and up to a year.

The metals of plates for fracture are typically stainless steel or other non-corrosive alloy. Attempts to fix posterior wall (PW) acetabular fractures using other commercially available plating systems are limited in two ways 1) These plates must be bent intra-operatively and contoured to fit the curvature of the patient's hip socket, and 2) often multiple plates are utilized to ensure stability to the reduced fracture. The problem with bending the plates during the surgery is that bleeding is ongoing until the incision is sutured closed and the procedure halts and this increases the patient's time under anesthesia which increases the rate of complications such as the need for blood transfusions and adverse reactions to anesthesia. The second problem with the current plating methods is that these methods use multiple plates and screws which increases the cost of the orthopaedic procedure to the patient, and the use of multiple plates is time consuming and this increases complication rates for the patient as noted above. The present invention provides faster and better stabilization of a posterior wall acetabular hip socket fracture by way of reducing fixation to a single plate and eliminating the need for intra-operative plate bending to fit the hip socket anatomy.

In bone surgeries, such as for fixation (i.e., fusion and unification of fractured bones) of reduced and realigned bones after a displaced bone fracture, the bones, in order for their mending and healing to occur, must be reduced and be kept held tightly together, so that they may not be dislocated or re-displaced before their fusion is complete. For this holding, steel plates have long been used, along with, depending on the situation, a variety of devices such as metal, plates, rods, hooks, bolts (pedicle screws) and the like. Recently an advancement in metal plate design produced an option for the metal bone screws to screw into the plate as well as the bone these newer plates are referred to as locking plates. This invention presented herein incorporates locking screw concepts with the added features of being pre-contoured to fit the hip socket curvature and the ability to buttress a fracture in this region with a single plate as opposed to using 2 or 3 plates. This invention presented herein incorporates limited contact plating concepts with the added features of being pre-contoured to fit the hip socket curvature without the need for further manipulation in the operating room (OR) and the ability to buttress a fracture in this region with a single plate as opposed to using 2 or 3 plates.

It is therefore an objective of the present invention to provide a bone binding construct capable of securing the hip socket posterior wall (PW) bone fracture while avoiding or greatly minimizing the operative time and expense of current fixation methods.

SUMMARY OF THE INVENTION

An improved posterior acetabular wall fracture buttress plate has a main plate and a plate extension. The buttress plate has a pair of arms extending from the main plate and an arm extending from the plate extension. The main plate and the plate extension are pre-contoured with a concavity contoured and bent lengthwise off horizontal relative to the main plate to mimic a hip socket contour posteriorly along an undersurface at about 38 degrees plus or minus 8 degrees to mimic a curvature of the hip to yield an angle on the undersurface of 142 degrees plus or minus 8 degrees. The arms are 1.0 cm or less wide. The plate extension extends from the main plate and has at least one transverse groove defining a breakaway section allowing the plate extension to be removed from the main plate.

The arm of the plate extension has a single slotted opening to receive a locking screw. Each of the pair of arms of the main plate has at least 2 holes for receiving bone screws and has a breakaway groove interposed between the 2 holes. The main plate of the buttress plate has at least seven locking screw options or holes for positional fixation of a posterior wall fracture fragment. The buttress plate is configured to buttress and inclined and angularly positioned relative to the hip contour to support a fracture surface area by having the contoured main portion sized to allow rotation of the buttress plate. The undersurface of the buttress plate has spikes or ridges or protrusions to provide bone contact. The spikes provide added fracture stability in fracture areas too small for screw fixation. The buttress plate is made of surgical grade stainless steel or other implantable material whether permanent or resorbable over time.

The improved posterior acetabular wall fracture buttress plate wherein the main plate of the buttress plate has 7 or more locking screw holes, and the arms have two or more screw holes. The arms have a length of 3 cm or greater.

The buttress plate allows for the following surgical procedure. A method of immobilizing a bone has the steps of: isolating a region of bone to be immobilized; reduction and temporary fixation of a plurality of fracture fragments with wires or reduction clamps; anatomic positioning of buttress plate in the best buttress position; drilling and measurement steps for selected screw placement; removal of provisional fixation devices including wires and clamps; intra-operative fluoroscopic imaging to confirm fracture reduction and suitable buttress plate positioning; and fixation of the screws. The method further has the step of stabilizing the bone in any and all situations of bone instability including, but not limited to situations of fracture, osteotomy, non-union and need or use for the bone binding including, but not limited to, the inclusion of metal plates or other hardware devices to achieve bone stabilization. The method further has the step of utilizing one or more metal plates or other hardware devices to stabilize the bone as indicated between different fracture patterns. The method further has the step of attaching the bone binding to the one or more metal plates or other hardware as indicated between different fracture patterns. The step of positioning the buttress plate in the best buttress position includes the buttress plate having a pair of arms extending from a main plate, the main plate being pre-contoured with a concavity contoured and bent lengthwise off horizontal relative to the main plate to mimic a hip socket contour posteriorly along an undersurface at about 38 degrees plus or minus 8 degrees to mimic a curvature of the hip to yield an angle on the undersurface of 142 degrees plus or minus 8 degrees. The arms being 1.0 cm or less wide. The main plate of the buttress plate has at least seven locking screw options or holes for positional fixation of a posterior wall fracture fragment.

A kit of buttress plates has a plurality of buttress plates; wherein the kit has at least one buttress plate with a small contoured curvature for smaller patients and at least one buttress plate with a larger contoured curvature for larger patients, the kit having a medium bend angle of 38 degrees off horizontal yielding an angle of 142 degrees. The larger buttress plate has a bend angle of 30 degrees off horizontal yielding an angle of 150 degrees. The smaller buttress plate has a bend angle of 45 degrees off horizontal yielding an angle of 135 degrees.

BRIEF DESCRIPTION OF THE IMAGES

The invention will be described by way of example and with reference to the accompanying drawings in which.

DETAILED DESCRIPTION OF THE INVENTION

Figure 1:
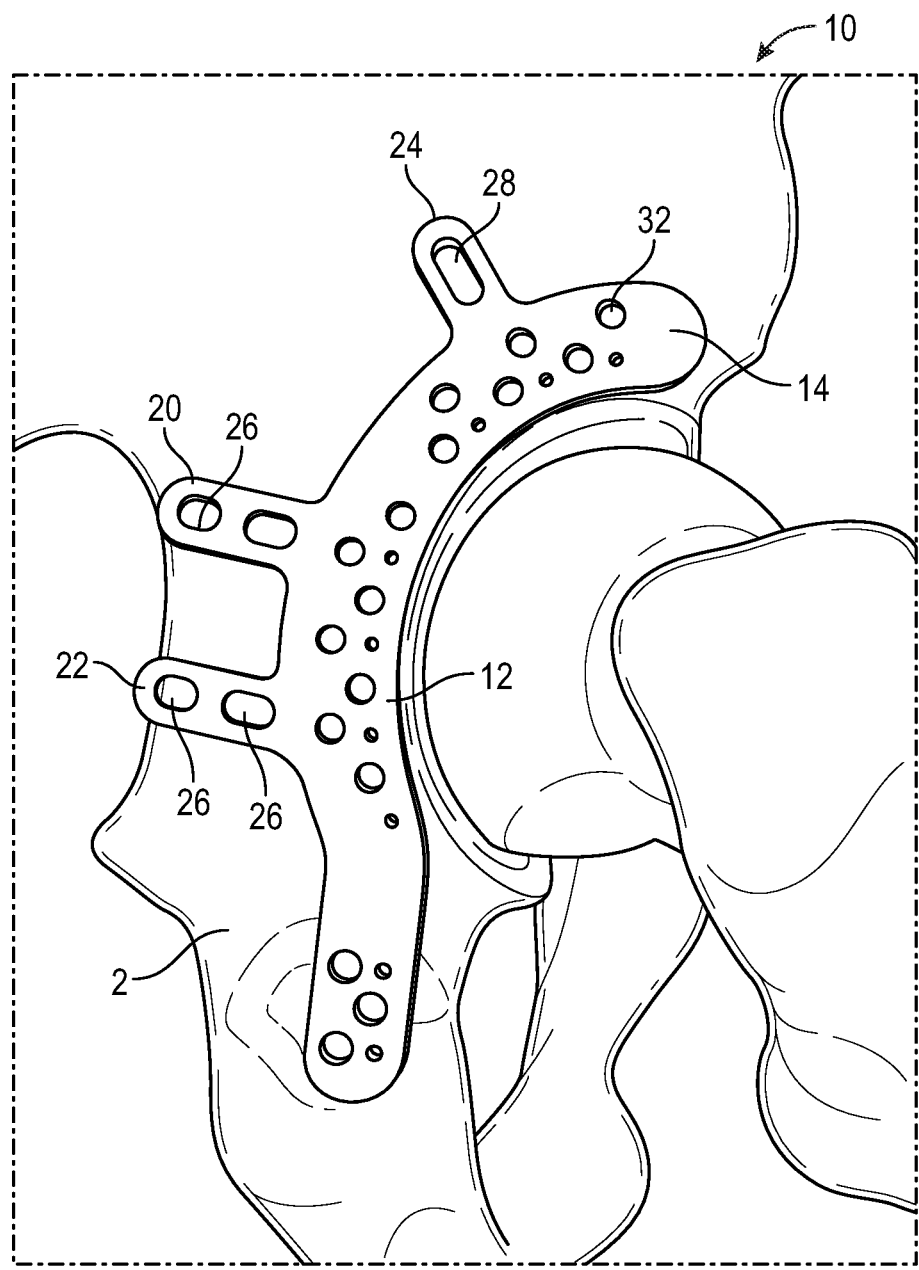
FIG. 1 is a perspective view of the Improved Pre-Contoured Buttress Plate For Posterior Wall Acetabular Fractures of the present invention shown positioned on a hip socket.

The present invention is an improved design of the Pre-Contoured Buttress Plate For Posterior Wall Acetabular Fractures described in related U.S. application Ser. No. 16/294,023 and related U.S. Pat. No. 10,307,192 both of which had the following features. The contents of both of the above are incorporated herein by reference in their entirety.

An improved bone plating for posterior hip socket fractures has locking screw capability for the posterior wall fragment, these locking screws which are directed and angled in such a way so as to avoid intra-articular placement. The hip socket has a defined concavity matching the size and shape of the femoral head. The posterior wall fragment locking screws of this invention are intended to avoid penetration of the femoral head and the hip joint. The length of screws to be placed in this region will vary and will be at the discretion of the surgeon. It is further conceived that an assortment of these pre-contoured plates will be made available in various lengths and widths to fit the myriad of posterior wall fracture patterns. The invention provides a method of immobilizing a posterior wall fracture or osteotomy or hardware for any and all hip socket reconstructive procedures and so forth having the steps of surgically isolating the region of the bone to be immobilized, binding the bone with a length of plating having discontinuous points of contact. Most metal plate designs for fractures incorporate scallops on the under surface of the plate for the purpose of limited plate contact to the bone as the plate is fixed to the bone with bone screws. The limited contact plate feature with undersurface scallops is preferably utilized in this new invention to allow for additional minor plate bending if required. The difference again in this plate is that it is pre-contoured and can achieve the same result as a combination of 2-3 plates with less risk of operative complications to the patient and less expense to the patient as well.

In one preferred embodiment, improved stand-alone bone plating implant or stand-alone buttress plate for Posterior Wall (PW) hip socket fractures has seven 2.8 mm locking screw options or holes for capturing the posterior wall fragment. These 7 screw options are directed medially towards the posterior column of the pelvis and angled in such a way so as to avoid intra-articular hip joint positioning or femoral head placement. The length of locking screws to be placed in this region will vary and would be at the discretion of the surgeon. The remainder of this buttress plate overlying the Posterior Wall and posterior column (PC) has the capability for 4-6 3.5 mm locking or non-locking screws. The hip socket has a defined concavity matching the size and shape of the femoral head. The length of all locking and non-locking screws to be placed in this buttress plate will vary and would be at the discretion of the treating surgeon. It is further conceived that an assortment of these pre-contoured buttress plates would be made available in a set of various lengths and widths to fit the myriad of posterior wall fracture patterns and to fit the slight differences in adult and pediatric anatomic dimensions. The present invention provides a method of immobilizing a posterior wall fracture or osteotomy or hardware for any and all hip socket reconstructive procedures and so forth having the steps of isolating the region of the bone to be immobilized, binding the bone with a length of plating having discontinuous points of limited bony contact, Most current plates designed for fractures incorporate scallops on the under surface of the plate for the purpose of reducing the area of contact between the plate and the bone it is fixed to with bone screws this plate continues that convention. This limited contact plate feature is preferably utilized in the preferred present invention to allow for additional minor plate bending if required. The difference again in this buttress plate is that it is pre-contoured to fit hip socket anatomy without the need for further manipulation in the OR and can achieve the same fracture buttressing effect that would result from a combination of a more expensive 2-3 plate construct. Furthermore, this is the first limited contact plate designed specifically in this shape with limited contact properties and the capacity for locking screws for repair of a PW fracture. This plate is designed and intended to be positioned over a fracture of the acetabular posterior wall and/or posterior column with the pre-contoured portion of the buttress plate juxtaposed to the hip socket margin posteriorly. Surgeons of fracture repair may find indications and application for this buttress plate elsewhere in the axial and appendicular skeleton. This is a stand-alone plate intended and designed to replace the typical 2 and 3 plate constructs used currently for these complex posterior acetabular fracture patterns. This buttress plate envisions several 0.5-1.0 mm additional smooth holes interposed in and around the (7) 2.8 mm locking holes these holes are for suture passage and hip capsular repair.

Turning to the present invention as illustrated in FIGS. 1-5, this Improved Pre-Contoured Buttress Plate For Posterior Wall Acetabular Fractures 10 has incorporated all of the features of the earlier design, but with added features to enhance its use.

Figure 2:
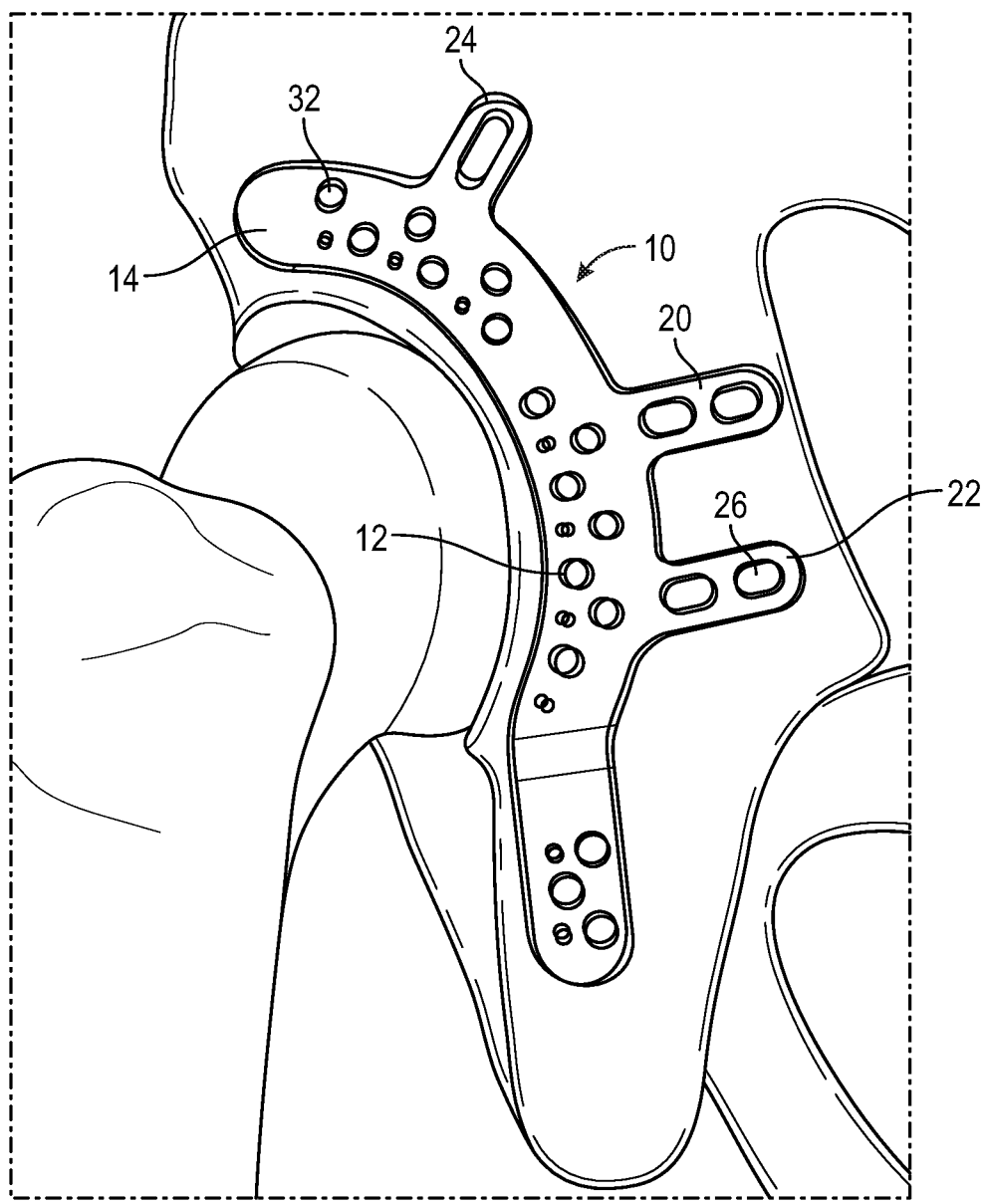
FIG. 2 is a perspective view of the Improved Pre-Contoured Buttress Plate For Posterior Wall Acetabular Fractures of the present invention shown positioned on an opposite hip socket.

With reference to FIGS. 1 and 2, the Improved Pre-Contoured Buttress Plate For Posterior Wall Acetabular Fractures 10 of the present invention is shown. In FIG. 1, the buttress plate 10 is shown attached over a hip socket 2 as illustrated. In FIG. 2, the opposite side hip socket 4 has the buttress plate 10 shown which is a mirror image of the opposite side buttress plate 10 shown in FIG. 1. Accordingly, when operating on a patient, the surgeon will select which hip he is working on and provide the appropriate buttress plate 10 for that hip configuration. In other words, there is a left side and right side plate 10 depending on the procedure being performed. The buttress plate 10 and each section 12, 14 have left and right hip socket designs, and may be used for either the left or right hip socket. Each of these plates have similar elements and components and are marked with identical reference numbers for facilitating and understanding of the invention as described herein.

With reference to FIGS. 1 and 2, each buttress plate 10 has a pair of arms 20, 22 extending from a main plate 12 and a plate extension 14 that has an extending arm 24. The main plate 12 and plate extension 14 are pre-contoured with a concavity contoured posteriorly along the undersurface at about 38 degrees plus or minus 8 degrees to mimic a curvature of a hip socket to yield an angle on the under surface of 142 degrees plus or minus 8 degrees. The plate extension 14 is an extension from the main plate 12 permitting fixation of acetabular fractures located superiorly. The arms 20, 22 and 24 respectively are one centimeter or less wide and bent lengthwise off horizontal from the main plate 12 and plate extension 14.

Each arm 20, 22 has a pair of holes 26 for receiving locking screws. Additionally, a plurality of holes 32 are positioned along the main plate 12 and plate extension 14 of the buttress plate 10. As shown, the plate extension 14 has an arm 24 with a single slotted opening 28. The slotted opening 28 allows for positioning of a fastener within the slot 28 to help secure the plate extension 14 to the bone of the hip socket 2, 4.

Figure 3:
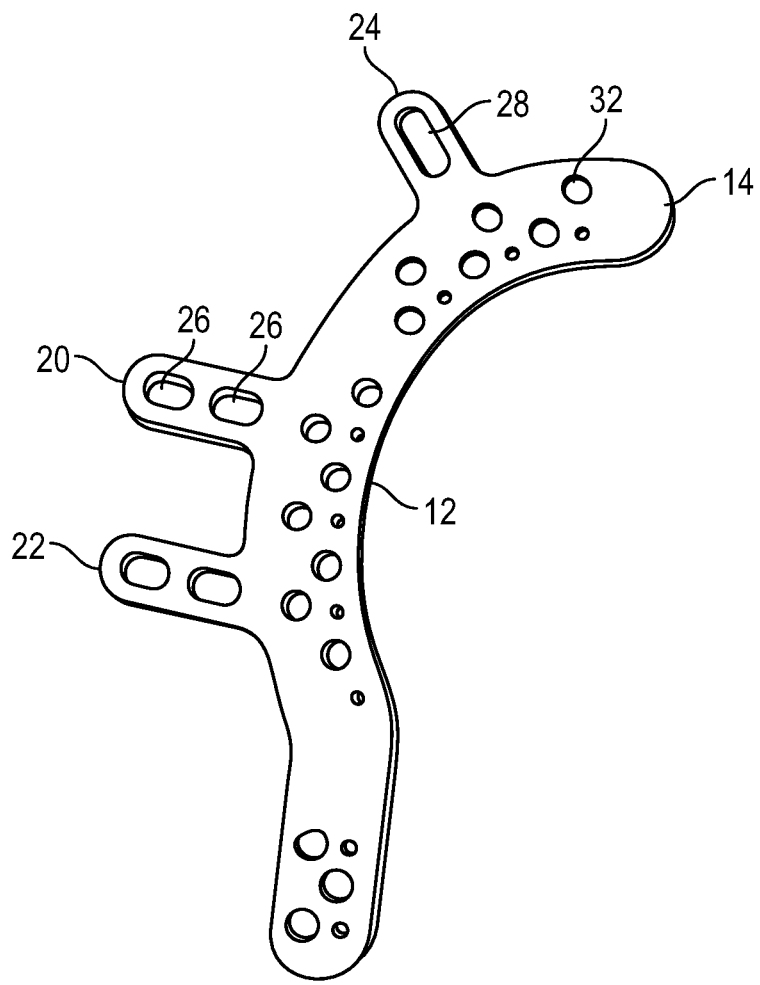
FIG. 3 is a perspective top or upper side view of the improved pre-contoured plate of the present invention take from FIG. 1.

With reference to FIG. 3, the top surface of the buttress plate 10 is illustrated. As shown, the main plate 12 and the plate extension 14 are curved and contoured as previously described. A pair of arms 20, 22 extending from the main plate 12 has the holes 26 illustrated. These arms 20, 22 are approximately 3 cm in length and approximately 1 cm wide.

Figure 4:
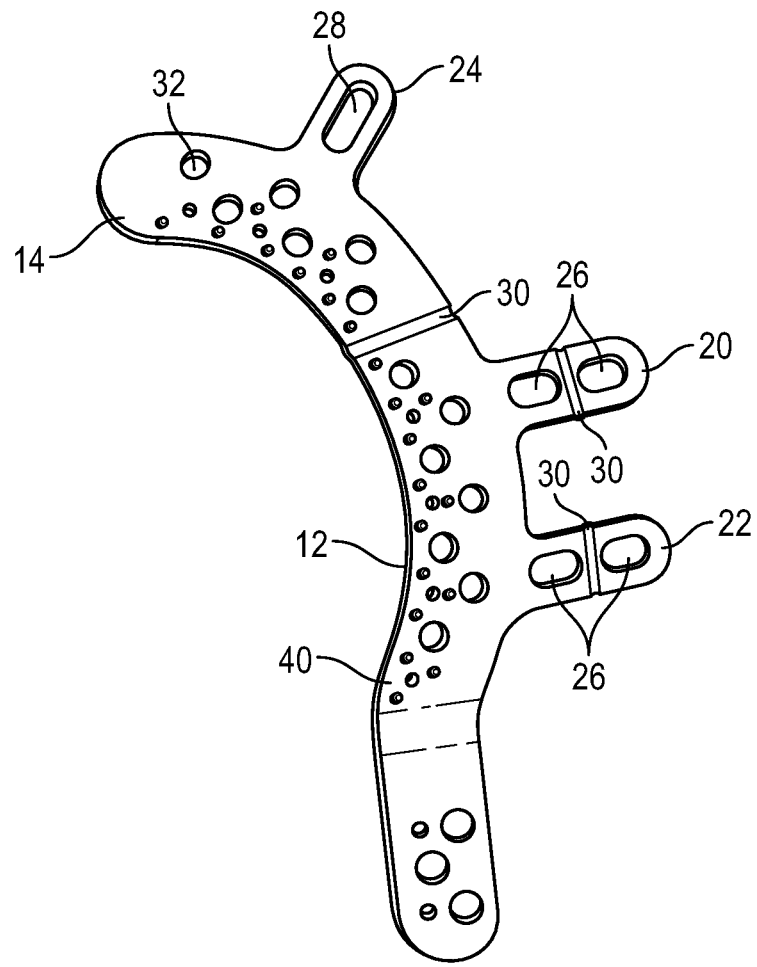
FIG. 4 is a perspective bottom or underside view of the improved pre-contoured plate of the present invention.

With reference to FIG. 4, the under side of the buttress plate 10 is illustrated. As shown, each of the pair of arms 20, 22 extending from the main plate 12 has a breakaway fracture groove 30 illustrated. The fracture grooves 30 extend transversely on the arms 20, 22 between the two holes 26 of each arm 20, 22. These fracture grooves 30 allow the arms 20, 22 to be broken between the hole openings 26 if so desired. This facilitates the placement of the plate 10 if needed by removing that portion of the arm 20, 22 that otherwise would have extended outwardly the full length of the arm 20, 22. This effectively reduces the arm length to about half or about 1.5 cm. With reference to the plate extension 14, there is also a transverse groove 30 extending across the buttress plate 10 between the main plate 12 and plate extension 14. This groove 30 is a breakaway groove that allows the plate extension 14 to be removed if so desired. The breakaway groves 30 permit further modularity to the buttress plate system 10 such that sections 12, 14 can be separated from each other allowing the buttress plate 10 to repair a combined posterior and superior acetabular fracture or an isolated posterior or superior acetabular fracture. Sections 12 and 14 can be used independently of each other. When the plate extension 14 is removed, the buttress plate 10 is shortened significantly with regard to its overall length. However, the buttress plate 10 will still retain the contoured main plate 12 to fit ideally on the hip socket contour. The lower half of section 12 is contoured to fit over the iscial tuberosity with screw fixation points through the plate.

As shown in FIG. 4, on the underside of the buttress plate 10, a plurality of projections in the form of bumps 40 are shown that keep the buttress plate 10 from being flush against the bone surface. The projections in the form of spikes 40 allow the plate 10 to be pushed into the bone locally to help secure the plate 10 in position as it is being fastened to the hip socket 2, 4. The spikes 40 provide added fracture stability in fracture areas too small for screw fixation.

Figure 5:
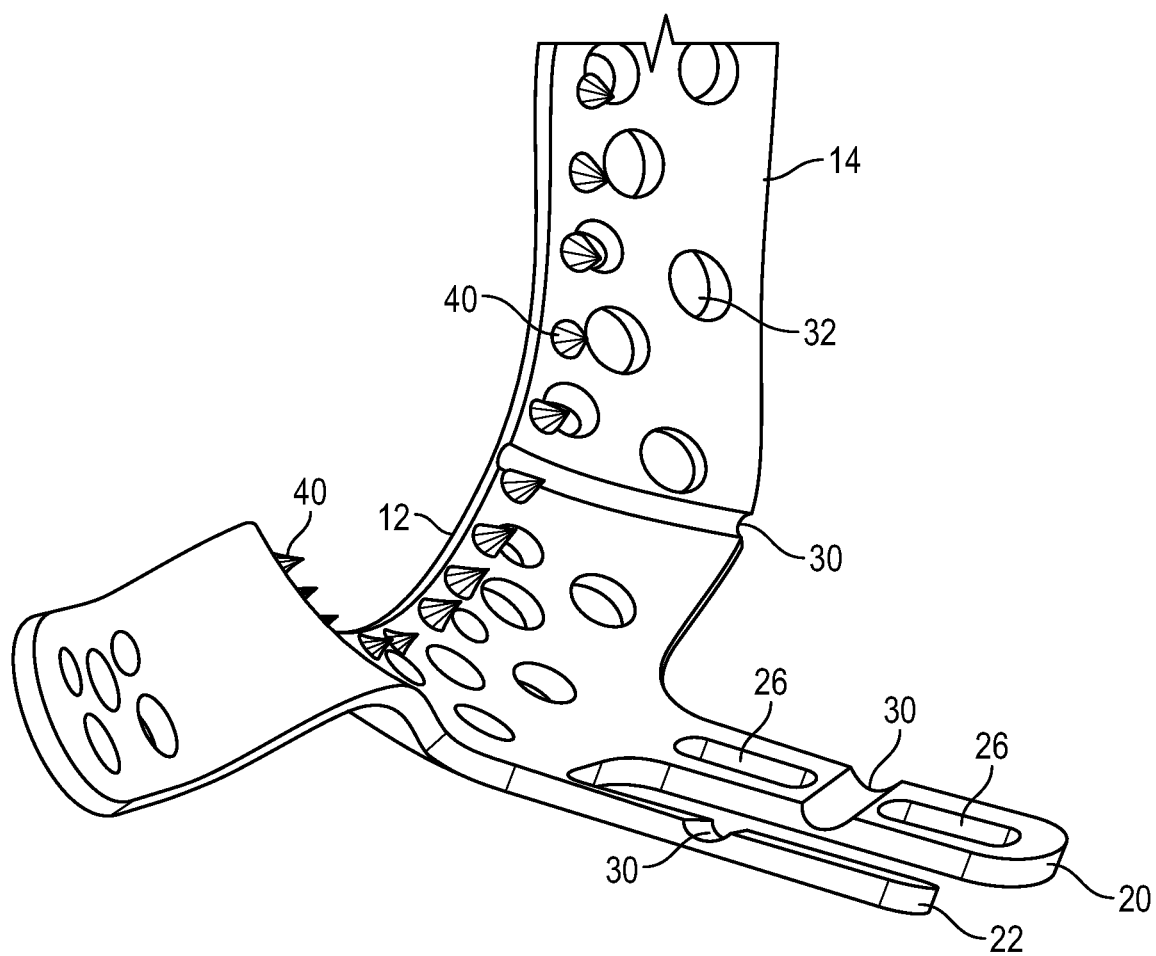
FIG. 5 is an enlarged view of the underside showing the contour of the plate, spikes and breakaway grooves.

With reference to FIG. 5, an enlarged view of a portion of the underside of the pre-contoured buttress plate 10 is shown to illustrate the projections in the form of bumps and spikes 40 and the undercut breakaway grooves 30.

A stand-alone pre-contoured buttress plate 10 with the capacity for (5-7) 2.8 mm locking screws 60 nearest the Posterior Wall fragment (4-6) 3.5 mm locking or non-locking screws 60 in the main plate and plate extension segments 12, 14 overlying the pelvic posterior column hip socket 2, 4. It is further conceived that an assortment of these pre-contoured buttress plates 10 would be made available as a kit in a set of various lengths and widths to fit the myriad of posterior wall fracture patterns and to fit the slight differences in adult and pediatric anatomic dimensions. One version of this plate 10 envisions 0.5-1.0 mm additional smooth holes interposed in and around the (7) 2.8 mm locking holes these holes would be for suture passage and hip capsular repair.

As shown in FIGS. 1-5, the buttress plate 10 has a main plate 12 with two arms 20, 22 extending generally perpendicular to the length of the main plate 12. As shown, the overall length of the main plate 12 is less than 4 cm, preferably about 3.8 cm. As shown, the buttress plate 10 has 16 holes 32 positioned therethrough to receive 2.7 mm or 2.8 mm locking screws. The holes 31, when formed as locking holes, have threads or are threaded. The arms 20, 22 are less than 1 cm wide, preferably 0.8 cm, and about 3 cm long or longer with 2 or more holes 26 in each for receiving 3.5 mm cortical screws. The buttress plate 10 is configured for stabilizing posterior wall acetabular fractures.

The contoured cavity of the main plate 12 has a curvature mimicking the surface contour of the hip 2, 4, preferably at a radius of bend slightly larger than the arc of the hip bone. This sizing allows the plate 10 to pivot angularly to accommodate a variety of fracture patterns and their inclined metal plate construct stabilization positions.

As shown, the underside has scallops or ridges or projections 40 to insure limited surface contact to the bone and to facilitate modest bending if slight adjustments are needed. Ideally, the curvature of the main plate 12 forms a 38 degree bend off horizontal, accordingly, a flat plate is 180 degrees while the preferred main plate 12 is bisected along a midline bent to 142 degrees, while the arms 20, 22 extend along the bend at the same inclination. This allows the buttress plate 10 to be positioned along a wide range of inclinations while still mimicking the posterior wall curvature. The thickness of the plate 10 is 3 mm or less allowing the arms 20, 22 to flex against the bone of the hip 2, 4 during fixation.

It is understood the plates 10 can be provided in a kit having a range of arm 20, 22, 24 lengths, preferably in 1 cm increments up to 10 cm and the number of holes 26, 28 increased from 2 holes for 3 cm, up to 6 or 8 holes depending on the length of the arm 20, 22, 24. Similarly, the kit of buttress plates 10 could have the main plate 12 be longer than 4 cm and wider than 1.5 cm. Each plate 10 increases in increments of 0.5 cm allowing for up to 8 cm in length and 3 cm in width, if so desired. Also, the kit can provide the bend of 38 degrees off horizontal yielding 142 degree inclination to be increased to a bend of 45 degrees or 135 degrees inclination for smaller patients and decreased to 30 degrees or 150 degrees inclination for larger patients. As such, the surgeon can select the optimum size for the patient and suitable to stabilize the fracture lines.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described which will be within the full intended scope of the invention as defined by the following appended claims.

The invention claimed is:

1. An improved posterior acetabular wall fracture buttress plate comprising:
   a buttress plate having a pair of arms extending from a main plate and a plate extension having an arm extending from the plate extension, the main plate and the plate extension being pre-contoured with a concavity contoured and bent lengthwise off horizontal relative to the buttress plate to mimic a hip socket contour posteriorly along an undersurface at 38 degrees plus or minus 8 degrees to mimic a curvature of the hip socket contour to yield an angle on the undersurface of 142 degrees plus or minus 8 degrees, the arms being 1.0 cm or less wide.

2. The improved posterior acetabular wall fracture buttress plate of claim 1 wherein the plate extension extends from the main plate and has at least one transverse groove defining a breakaway section allowing the plate extension to be removed from the main plate.

3. The improved posterior acetabular wall fracture buttress plate of claim 2 wherein the arm of the plate extension has a single slotted opening to receive a locking screw.

4. The improved posterior acetabular wall fracture buttress plate of claim 1 wherein the main plate of the buttress plate has at least seven locking screw options or holes for positional fixation of a posterior wall fracture fragment.

5. The improved posterior acetabular wall fracture buttress plate of claim 1 wherein the buttress plate is configured to buttress and inclined and angularly positioned relative to the hip socket contour to support a fracture surface area by having a contoured main portion sized to allow rotation of the buttress plate.

6. The improved posterior acetabular wall fracture buttress plate of claim 1 wherein the undersurface of the buttress plate has spikes or ridges or protrusions to provide bone contact.

7. The improved posterior acetabular wall fracture buttress plate of claim 1 wherein the buttress plate is made of surgical grade stainless steel or other implantable material whether permanent or resorbable over time.

8. The improved posterior acetabular wall fracture buttress plate of claim 1 wherein each arm of the pair of arms of the main plate has at least 2 holes for receiving bone screws.

9. The improved posterior acetabular wall fracture buttress plate of claim 1 wherein the main plate of the buttress plate has 7 or more locking screw holes and the arms have two or more screw holes.

10. The improved posterior acetabular wall fracture buttress plate of claim 1 wherein the arms have a length of 3 cm or greater.

11. A method of immobilizing a bone comprising the steps of:
    isolating a region of bone to be immobilized;
    reduction and temporary fixation of a plurality of fracture fragments with wires or reduction clamps;
    anatomic positioning of a buttress plate having a main plate and an extension plate in a best buttress position;
    drilling and measurement steps for selected screw placement;
    removal of provisional fixation devices including wires and clamps;
    intra-operative fluoroscopic imaging to confirm fracture reduction and suitable buttress plate positioning; and
    fixation of screws.

12. The method of claim 11 further comprising the step of:
    stabilizing the bone in any and all situations of bone instability including, but not limited to situations of fracture, osteotomy, non-union and need or use for a bone binding including, but not limited to, inclusion of metal plates or other hardware devices to achieve bone stabilization.

13. The method of claim 12 further comprises the step of:
    utilizing one or more metal plates or other hardware devices to stabilize the bone as indicated between different fracture patterns.

14. The method of claim 13 further comprises the step of:
    attaching the bone binding to the one or more metal plates or other hardware as indicated between different fracture patterns.

15. The method of claim 11 wherein the step of positioning the buttress plate in the best buttress position includes the buttress plate having a pair of arms extending from a main plate.

16. The method of claim 15 wherein the arms being 1.0 cm or less wide and the main plate and extension plate are pre-contoured with a concavity contoured and bent lengthwise off horizontal to mimic a hip socket contour posteriorly along an undersurface at 38 degrees plus or minus 8 degrees to mimic a curvature of the hip socket contour to yield an angle on the undersurface of 142 degrees plus or minus 8 degrees.

17. The method of claim 16 wherein the main plate of the buttress plate has at least seven locking screw options or holes for positional fixation of a posterior wall fracture fragment.

18. A kit of buttress plates comprises:
    a plurality of buttress plates;

wherein the kit has at least one buttress plate with a small contoured curvature for smaller patients and at least one buttress plate with a larger contoured curvature for larger patients, the kit having a medium bend angle of 38 degrees off horizontal yielding an angle of 142 degrees.

19. The kit of claim 18 wherein the larger buttress plate has a bend angle of 30 degrees off horizontal yielding an angle of 150 degrees.

20. The kit of claim 18 wherein the smaller buttress plate has a bend angle of 45 degrees off horizontal yielding an angle of 135 degrees.

* * * * *